(12) United States Patent
Arai (10) Patent No.: US 8,545,767 B2
(45) Date of Patent: Oct. 1, 2013

(54) PASSIVE ONE-WAY VALVE AND MICROFLUIDIC DEVICE

(75) Inventor: Susumu Arai, Tokyo (JP)

(73) Assignee: Sumitomo Bakelite Co., Ltd., Tokyo (JP)

( * ) Notice: Subject to any disclaimer, the term of this patent is extended or adjusted under 35 U.S.C. 154(b) by 599 days.

(21) Appl. No.: 12/160,593

(22) PCT Filed: Jan. 9, 2007

(86) PCT No.: PCT/JP2007/050078
§ 371 (c)(1),
(2), (4) Date: Jul. 10, 2008

(87) PCT Pub. No.: WO2007/080850
PCT Pub. Date: Jul. 19, 2007

(65) Prior Publication Data
US 2010/0166610 A1   Jul. 1, 2010

(30) Foreign Application Priority Data
Jan. 12, 2006   (JP) ................................ 2006-004318

(51) Int. Cl.
*G01N 21/75* (2006.01)
(52) U.S. Cl.
USPC ............. 422/417; 422/50; 422/500; 422/501; 422/503; 422/531; 436/180; 137/67; 137/601.04
(58) Field of Classification Search
USPC ................... 422/50, 417, 537, 500–503, 531; 137/67, 601.04; 436/180
See application file for complete search history.

(56) References Cited

U.S. PATENT DOCUMENTS 3,601,152 A * 8/1971 Kenworthy .................... 137/843
6,523,559 B2 * 2/2003 Beebe et al. ...................... 137/3

FOREIGN PATENT DOCUMENTS

| JP | 2000-027813 | 1/2000 |
| JP | 2001-304440 | 10/2001 |

OTHER PUBLICATIONS

Unger, Marc A. et al., "Monolithic Microfabricated Valves and Pumps by Multilayer Soft Lithography", Science, vol. 288, pp. 113-116 (Apr. 7, 2000).

* cited by examiner

*Primary Examiner* — Jyoti Nagpaul
(74) *Attorney, Agent, or Firm* — Nixon Peabody LLP (57) ABSTRACT

This passive one-way valve is used in a connection portion between first and second flow channels, and includes: an inlet portion into which a fluid from the first flow channel flows; an elastic portion for blocking the inlet portion; a rigid portion for supporting the elastic portion from a side opposite to the inlet portion across the elastic portion; a gap portion formed around the rigid portion; and an outlet portion which is in communication with the gap portion for letting the fluid flow out into the second flow channel. Furthermore, the inlet portion is hermetically sealed by the elastic portion being pressed against the inlet portion side by the rigid portion. According to this passive one-way valve, it is possible to provide a simple and inexpensive passive one-way valve without requiring special equipment such as a vacuum pump and pressurized air, and to provide a microfluidic device using the same.

17 Claims, 4 Drawing Sheets

PASSIVE ONE-WAY VALVE AND MICROFLUIDIC DEVICE

CROSS REFERENCE TO RELATED APPLICATIONS OR PRIORITY CLAIM

This application is a national phase of International Application No. PCT/JP2007/050078, entitled "PASSIVE ONE-WAY VALVE AND MICROFLUIDIC DEVICE", which was filed on Jan. 9, 2007, and which claims priority of Japanese Patent Application No. 2006-004318, filed Jan. 12, 2006.

TECHNICAL FIELD

The present invention relates to a microfluidic device with a micro fluid control mechanism in which a structure such as a fine flow channel, a reaction vessel, an electrophoresis column, and a membrane separation mechanism is formed. More particularly, the present invention relates to a microfluidic device useful as, for example: a micro reaction device (micro reactor) for wide use in chemistry, biochemistry, etc.; an integrated DNA analysis device; a micro electrophoresis device; a micro analysis device such as a micro chromatography device; a micro device for use in assay sample preparation such as mass spectroscopic analysis and liquid chromatography; and a device for use in a physical and chemical treatment such as extraction, membrane separation, and dialysis. Furthermore, the present invention relates to a microfluidic device with a function of a passive one-way valve which is inexpensive and highly reliable with a combination of an elastic portion and a rigid portion.

BACKGROUND ART

Recently, an increasing amount of research has been focused on micro-sizing of systems for a chemical reaction and separation called a micro reactor and a micro total analysis system (μTAS) where a micromachining technology is utilized. These systems are expected to be applied to the analysis and synthesis of nucleic acids, proteins, sugar chains, etc., to the speedy analysis of trace chemical substances, and to high throughput screening of medical products and drugs, which are performed on a microchip with microchannels (extremely thin flow channels).

Such micro-sizing of a system has advantages including: (1) the consumption and waste of samples and reagents used in a chemical reaction and an antigen-antibody reaction can be reduced in quantity; (2) the power source necessary for a process can be reduced; (3) the increase in the ratio of surface area to volume can speed up heat transfer and substance transfer, and hence expectable results are: accurate control of reaction and separation; speeding up and promotion of high efficiency; and suppression of side reactions; (4) a multitude of samples can be handled on the same substrate; and (5) steps from sampling to detection can be performed on the same substrate. As a result, an actualization of a space-saving, portable, and inexpensive system can be conceived.

On the other hand, such micro-sizing of a system has disadvantages including: (1) detection sensitivity decreases in many cases due to a decrease in detection area; (2) it is difficult to generate a turbulent flow in a micro-scale fluid flow, and hence when reagents and the like is mixed, the mixture is dispersive, which takes time be well mixed; and (3) if bubbles or the like is generated, it is difficult to remove them due to an influence of surface tension, often leading to a tremendous influence on a measurement system.

With these advantages and disadvantages, microfluidic technology has been examined, and has been applied to: an acceleration sensor, a pressure sensor, a position sensor (gyroscope) and the like in the field of the automobile industry; a light guide, an optical switch, a minor, a lens, and the like in the field of telecommunication; and blood analysis, DNA analysis, chemical crime investigation, and the like in the field of life science. As a result, microfluidic technology has come to be found in our daily lives. In addition, it has been further applied to the fields of food, environmental testing, and ammunition.

The microfluidics technology currently under development is for application to sensors in many cases. Reported examples of such sensors include micro sensors which utilize: an immunoenzymatic reaction or antigen-antibody reaction; an ion-sensitive field effect (ISFET); a microelectrode; a microcantilever; acoustic waves; and resonance. Often reported examples of applications thereof include: a micro electrophoresis chip; a micro PCR (Polymerase Chain Reaction) chip; a micro gas chromatography chip; a micro liquid chromatography chip; and a DNA separation chip. Furthermore, the development of Lab-on-a-Chip in which the steps from sampling to analysis are performed on the same chip has been reported. Examples of this include: a multi-functional biochip using a nucleic acid or antibody specific to anthrax bacteria and coli bacilli; a portable measurement instrument for monitoring glucose, lactose, etc.; and laboratory test chip using an antigen-antibody reaction.

In fabricating a microfluidic device as described above, it is necessary to control the flow of fluids, for example to flow, stop, or one-directionally flow a plurality of micro fluids.

Non-Patent Document 1 describes a microfluidic device including: a liquid flow channel formed of silicone rubber; and a pressurization gap portion which is formed so as to be separated from the flow channel by a separation wall of silicone rubber. In addition, it describes an active fluid control method in which pressurized air is introduced into the pressurization gap portion to deflect the silicone rubber separation wall into the flow channel side, and with this deflection, the cross-sectional area of the flow channel is changed to thereby control the flow of a liquid.

However, this microfluidic device is made of a flexible material with low rigidity. Therefore, disadvantages arise such as it is difficult to manufacture a thin device because the material is low in pressure resistance and excessive in flexibility, and the device becomes complicated because it is an active device which requires a signal from the outside.

The micro valve described in FIG. 1 of Patent Document 1 includes: a thick, first pipe; a plurality of thin pipes which are formed thinner than the first pipe, one end of the thin pipes being connected so as to be in communication with the first pipe; and a second pipe which is formed thicker than the thin pipe and is connected so as to be in communication with the other end of the thin pipes, in which internal walls of the thin pipes are formed to be hydrophobic. According to this micro valve, when a liquid is introduced into the first pipe, the position of the liquid in the first pipe can be optionally controlled depending on a pressure difference between the pressure on the first pipe side and the pressure on the second pipe side across the liquid as a boundary. However, in the micro valve of Patent Document 1, it is very difficult to form a plurality of thin pipes. In addition, there is also a possibility that the thin pipe will be damaged if the pressure difference is too large. Moreover, a treatment to make these thin pipe portions specifically hydrophobic is also very difficult. Furthermore, the thin pipes of Patent Document 1 do not exert a function as a check valve, and cannot generate a pressure difference without using a pump.

The micro valve described in FIG. 3 of Patent Document 2 includes a valve mechanism formed of two micro flow channel chips made of polydimethylsiloxane (PDMS) and one membrane, in which the membrane undergoing displacement in a valve region is attached to and detached from a valve seat to thereby open and close a working fluid channel. Furthermore, in this micro valve, a drive fluid channel with a pressure chamber on which a pressure of a drive fluid acts in the valve region is formed by attachment to the membrane. It is configured such that the membrane is displaced by supply and exhaust of the pressure of the drive fluid to and from the pressure chamber to be attached to and detached from the valve seat, to thereby open and close as a one-way valve. However, in the micro valve described in Patent Document 2, the membrane which is attached to and detached from the valve seat is one-directionally displaced only toward the pressure chamber. Therefore, the gap between the membrane and the valve seat when the valve is opened is insufficient, and hence fluidity of the fluid is low. This is a cause of the occurrence of a pulsating flow. In addition, the pressure of the drive fluid is supplied from a vacuum pump via a glass pipe, making all of the equipment complicated and expensive.

Non-Patent Document: SCIENCE (Vol. 288, pp. 113-6 (2000))

Patent Document 1: Japanese Unexamined Patent Publication, First Publication No. 2000-27813

Patent Document 2: Japanese Patent No. 3418727

DISCLOSURE OF INVENTION

An object of the present invention is to provide a simple and inexpensive passive one-way valve without requiring special equipment such as a vacuum pump and a pressurized air, and to provide a microfluidic device using the same.

The present invention provides a passive one-way valve for use in a connection portion between first and second flow channels, including: an inlet portion into which a fluid from the first flow channel flows; an elastic portion for blocking the inlet portion; a rigid portion for supporting the elastic portion from a side opposite to the inlet portion across the elastic portion; a gap portion formed around the rigid portion; and an outlet portion which is in communication with the gap portion for letting the fluid flow out into the second flow channel, in which the inlet portion is hermetically sealed by the elastic portion being pressed against the inlet portion by the rigid portion.

In this passive one-way valve, it is preferable that the elastic portion be made of a material with a tensile elastic modulus of 0.1 MPa or more and 700 MPa or less, and that the rigid portion be made of a material with a tensile elastic modulus of 0.5 GPa or more.

Furthermore, it is preferable that the elastic portion be pressed by the rigid portion over an area 0.5 or more times and 1.5 or less times that of an opening portion of the inlet portion.

Furthermore, it is preferable that the rigid portion has a cylindrical, spherical, or hemispherical shape.

Furthermore, it is preferable that the elastic portion have a thickness of 50 µm or more and 2000 µm or less.

Furthermore, it is preferable that an elastic deformation amount of the elastic portion caused by the elastic portion being pressed by the rigid portion be 10 µm or more and 500 µm or less with respect to a pressed direction.

Furthermore, the present invention provides a microfluidic device having a plurality of flow channels in communication with one another in a connection portion, in which the connection portion is provided with any of the above-mentioned passive one-way valves.

It is preferable that a base material of the microfluidic device be made of a plastic.

Furthermore, a physiologically active substance which includes at least one of nucleic acid, protein, a sugar chain, and glycoprotein may be immobilized in part of the micro flow channel of this microfluidic device.

In this case, the physiologically active substance is immobilized in, for example, the flow channel which is in communication with the inlet portion of the passive one-way valve.

By use of the present invention, it is possible to provide a simple and inexpensive passive one-way valve without requiring special equipment such as a vacuum pump or pressurized air, and to provide a microfluidic device using the same.

DESCRIPTION OF THE REFERENCE SYMBOLS

1: base material
2: inlet
3, 12: microchannel (first flow channel)
4, 14: microchannel (second flow channel)
6: elastic portion
5, 5a, 5b: rigid portion
7: outlet
8: one-way valve inlet portion
9: valve chamber
10: one-way valve outlet portion
11: elastic deformation amount along pressed direction of elastic portion
D1, D2: diameter of rigid portion
P: protrusion amount of rigid portion
S1, S2: gap portion
V: passive one-way valve
W1: thickness of elastic portion
W2: thickness of valve chamber

BEST MODE FOR CARRYING OUT THE INVENTION

Hereunder is a description of a best mode for carrying out the invention by using the drawings.

Figure 1:
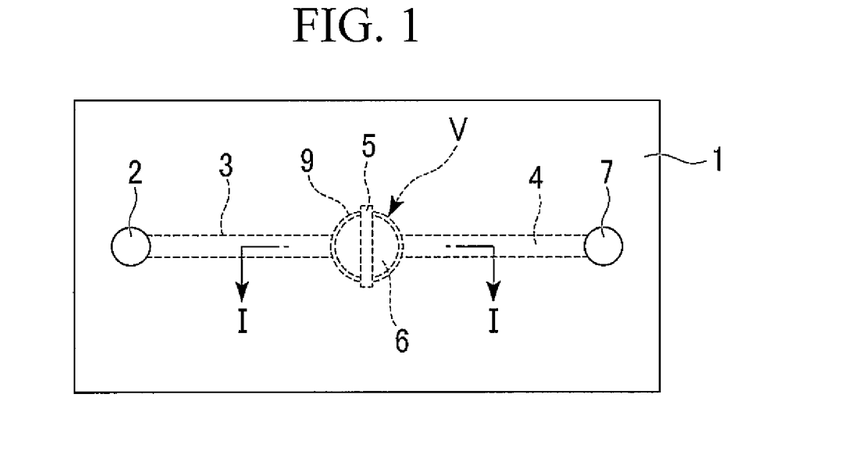
FIG. 1 is a plan view showing a first embodiment of a microfluidic device with a passive one-way valve of the present invention.
Figure 2:
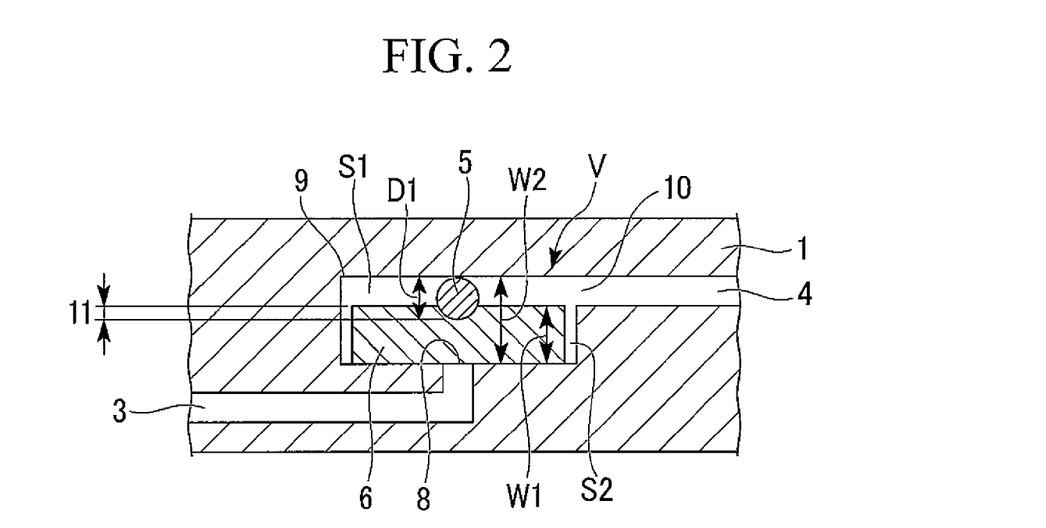
FIG. 2 is a cross-sectional view of FIG. 1 taken along the line I-I.

FIG. 1 is a plan view showing an outline of one embodiment of a microfluidic device using a passive one-way valve of the present invention. FIG. 2 shows a cross-sectional view of FIG. 1 taken along the line I-I. The microfluidic device shown in FIGS. 1 and 2 includes: a basic structure as a microfluidic device which is provided with an inlet 2 and outlet 7 respectively opening at both ends in the longitudinal direction (left and right direction of the figure) of a base material 1 and with microchannels 3 and 4 as first and second flow channels which connect the inlet 2 with the outlet 7; and a passive one-way valve V provided in a connection portion between the microchannels 3 and 4.

The microchannels 3 and 4 extend inside the base material 1 in the longitudinal direction of the base material 1. The microchannel 3 connecting to the inlet 2 is positioned on one end side (on the lower side in FIG. 2; hereinafter referred to as "one end side" for short) in a thickness direction (up and down direction of FIG. 2) of the base material 1. The microchannel 4 connecting to the outlet 7 is positioned on one end side (on the upper side in FIG. 2; hereinafter referred to as "the other end side" for short) in the thickness direction of the base material 1.

The passive one-way valve V is provided between the microchannels 3 and 4, and includes: an elastic portion 6; a rigid portion 5; a one-way valve inlet portion 8; a valve chamber 9; and a one-way valve outlet portion 10. The valve chamber 9 is a cylindrical shaped space formed in the central portion in the longitudinal direction of the base material 1, around an axis extending in the thickness direction of the base material 1. It is coupled to the microchannel 3 via the one-way valve inlet portion 8 opening in the central portion on one end side thereof, and is coupled to the microchannel 4 via the one-way valve outlet portion 10 opening in the side surface on the other end side thereof.

The one-way valve inlet portion 8 is blocked by one end surface of the disc-like elastic portion 6 which is arranged in the valve chamber so as to be coaxial with the valve chamber 9. The round-rod-like rigid portion 5 which crosses the valve chamber 9 along the radial direction thereof abuts on the other end surface of the elastic portion 6, so as to cross the elastic portion 6 along the radial direction thereof. The rigid portion 5 is supported from the other end side by the base material 1 so as to be prevented from moving to the other end side. It causes its side surface abutting on the elastic portion 6 to dent into the other side surface of the elastic portion 6 to deform the elastic portion 6 along the thickness direction thereof. Thus, it presses the elastic portion 6 against the one-way valve inlet portion 8 with a predetermined pressure. That is, in this passive one-way valve V, the sum total of a diameter D1 of the rigid portion 5 and a thickness W1 of the elastic portion 6 is set to be larger than a thickness W2 of the valve chamber 9.

Furthermore, the thickness W1 of the elastic portion 6 is formed a little thinner than the thickness W2 of the valve chamber 9, and the diameter of the elastic portion 6 is formed a little smaller than that of the valve chamber 9. As a result, a gap portion S1 in communication with the one-way valve outlet portion 10 is formed on the other end side of the elastic portion 6 placed in the valve chamber 9, and a gap portion S2 in communication with the gap portion S1 is formed around the elastic portion 6 placed in the valve chamber 9.

A fluid having flowed into the microchannel 3 from the inlet 2 flows in the outlet 7 direction (the forward direction) via the passive one-way valve V and the microchannel 4, but does not flow in the inlet 2 direction (the backward direction) from the outlet 7. This is due to the function of the passive one-way valve V. That is, in the case where the fluid flows in the forward direction, an edge portion of the elastic portion 4 pressed by the rigid portion 5 is elastically deformed into the other end side by the pressure of the fluid to be pressed up into the gap portion S1. This generates a gap through which the fluid flows between the one-way valve inlet portion 8 and the gap portion S2. As a result, the fluid flows in the outlet 7 direction via the one-way valve inlet portion 8, the gap portions S2 and S1, and the one-way valve outlet portion 10. On the other hand, in the case where the fluid is about to be flowed in the backward direction, no gap through which the fluid flows is generated between the one-way valve inlet portion 8 and the gap portion S2 because the elastic portion 6 is pressed by the rigid portion 5. As a result, the fluid does not flow in the backward direction. In this case, even if the pressure on the outlet 7 side is increased, the fluid will not flow because the force in the direction of pressing the elastic portion 6 against the one-way valve inlet portion 8 is increased.

For a material of the base material 1 of the microfluidic device, S1, glass, plastic, or the like may be used. The inlet 2, the outlet 7, the microchannels 3 and 4, and the like are machined in the base material 1. This machining method is optional, and a method such as a cutting work, an injection molding, a solvent casting method, photolithography, laser abrasion, and a hot embossing method may be used.

It is required that the elastic portion 6 be made of a member with a tensile elastic modulus of 0.1 MPa or more and 700 MPa or less, preferably 0.5 MPa or more and 500 MPa or less. In the case of a tensile elastic modulus of less than 0.1 MPa, the elastic portion 6 is too soft. Therefore, an elastic force (pressure) may not be obtained which is strong enough to block the one-way valve inlet portion 8 even if the elastic portion 6 is pressed by the rigid portion 5. It is possible to maintain hermeticity with respect to the one-way inlet portion 8 by increasing a pressing amount by the rigid portion 5. However, this makes the device thicker, and hence is not economical. If the elastic portion 6 has a tensile elastic modulus of more than 700 MPa, there is a possibility that tight contact when the elastic portion 6 is pressed against the one-way valve inlet portion 8 by the rigid portion 5 is decreased, making it difficult to hermetically seal the one-way valve inlet portion 8 along its shape. In actuality, the surface of machined goods for the microchannel has asperities. Therefore, to hermetically seal the one-way valve inlet portion 8 at a level allowing no fluid to flow through at all, it is necessary to bring the elastic portion 6 in sufficiently tight contact with the one-way valve inlet portion 8 to the shape thereof. Although the degree of hermetic sealing is increased with the increase in pressing amount by the rigid portion 5, this is not practical because a considerable amount of pressure is required when the fluid is flowed in the forward direction.

The material for the elastic portion 6 is not particularly limited as long as it has a tensile elastic modulus of 0.1 MPa or more and 700 MPa or less. Examples of preferably usable materials include silicone rubber, isoprene rubber, butadiene rubber, nitrile rubber, PDMS, fluorocarbon rubber, and polyurethane rubber. Furthermore, the shape of the elastic portion 6 is preferably a sheet because of its easy workability. However, molded products with the shape of a plate, a coating film, a rod, a tube, a protrusion, or other complicated shapes pose no particular problems, and hence any shape suitable for the shape of the one-way valve inlet can be selected among them.

It is preferable that a material with a tensile elastic modulus of 0.5 GPa or more be used for the rigid portion 5. More preferable tensile elastic modulus is 0.7 MPa or more. With a tensile elastic modulus of less than 0.5 GPa, the rigid portion 5 cannot effectively press the elastic portion 6. An upper limit value of the tensile elastic modulus of the rigid portion 5 is not particularly limited as long as the rigid portion 5 is not damaged or deformed by the pressure of the fluid or a repulsive force from the elastic portion 6. The material for the rigid portion 5 is not particularly limited as long as it has a tensile elastic modulus of 0.5 GPa or more. Examples of preferably usable materials include: metal such as steel, stainless steel, brass, copper, and aluminum; plastic such as nylon, polyethylene, fluorine, cycloolefin, PEEK, PES, PP, Fluorocarbon, PI, and PE; and glass.

It is preferable that gap portion S1 formed inside the valve body 9 be as small as possible. However, if the gap portion S1 is too small, the space in which the elastic portion 6 is displaced when the fluid flows in the forward direction becomes small accordingly, making it difficult for the fluid to flow. Furthermore, the elastic portion 6 is pressed around the one-way valve inlet portion 8 by the rigid portion over a predetermined area. This area is preferably 0.5 or more times and 1.5 or less times, more preferably 0.7 or more times and 1.3 or less times that of the opening portion of the one-way valve inlet portion 8. If this area is less than 0.5 times that of the opening portion, the force of the elastic portion 6 pressing the one-way valve inlet portion 8 is weak, and hence there may be a decrease in hermeticity with respect to the one-way valve inlet portion 8. If this area is more than 1.5 times that of the opening portion, the elastic portion 6 ceases to function as a valve.

Figure 3:
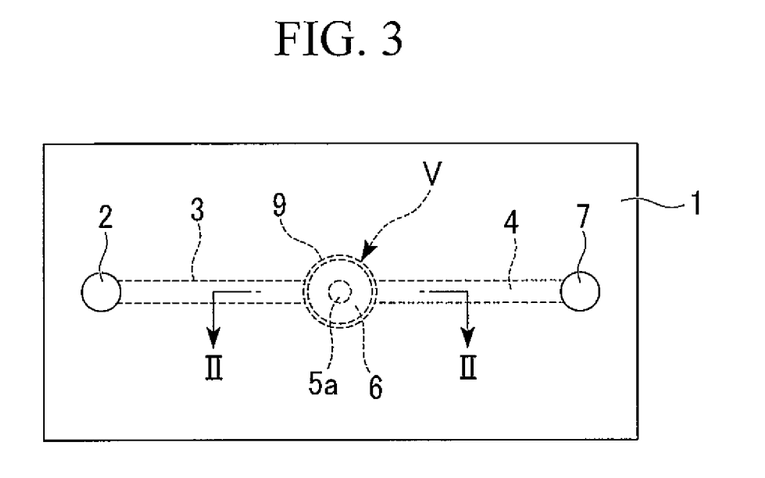
FIG. 3 is a plan view showing a second embodiment of a microfluidic device with a passive one-way valve of the present invention.
Figure 4:
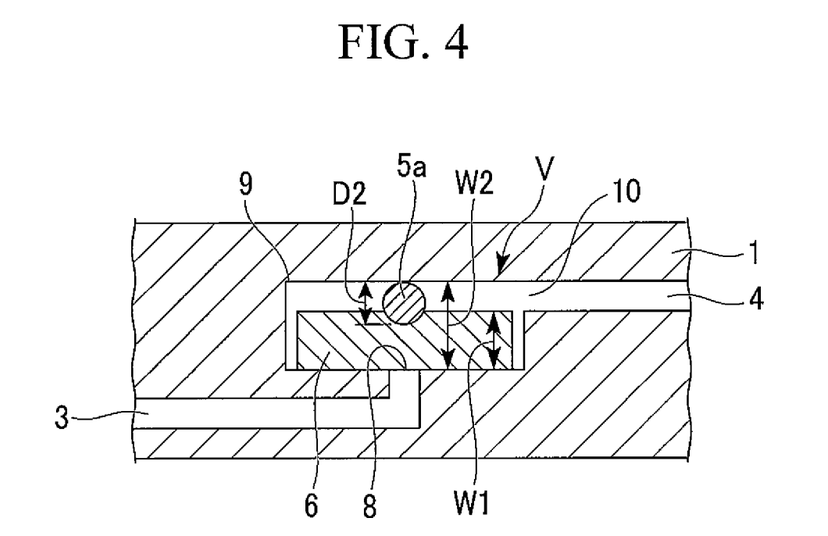
FIG. 4 is a cross-sectional view of FIG. 3 taken along the line II-II.
Figure 5:
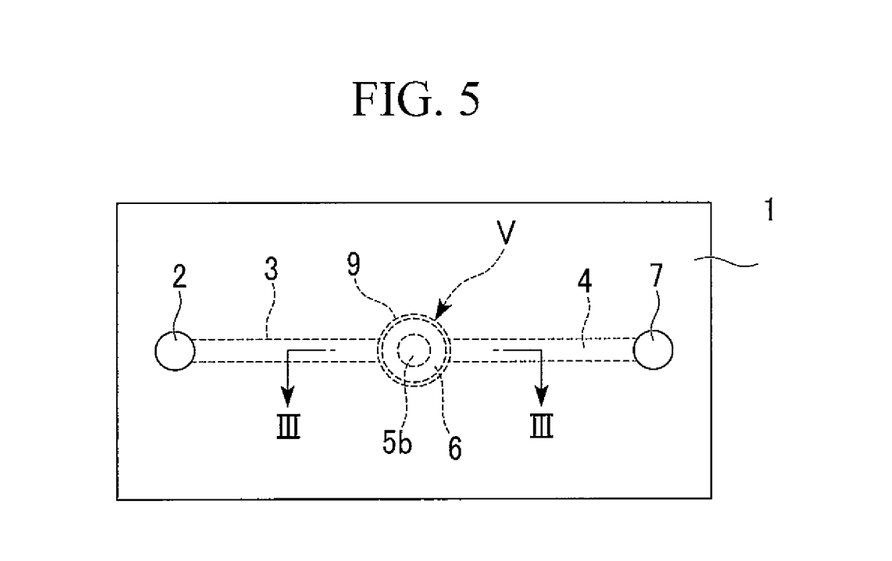
FIG. 5 is a plan view showing a third embodiment of a microfluidic device with a passive one-way valve of the present invention.
Figure 6:
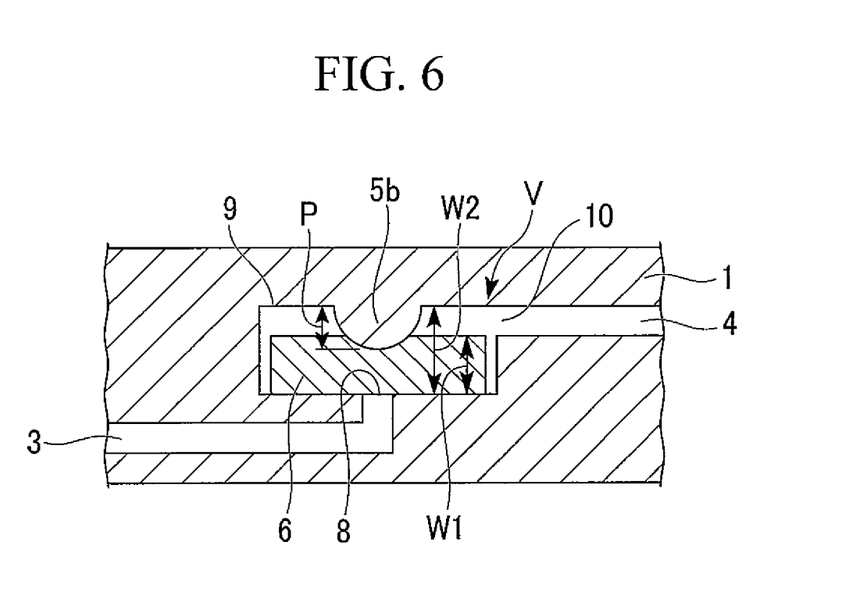
FIG. 6 is a cross-sectional view of FIG. 5 taken along the line III-III.

The most practical and effective shape of the rigid portion 5 is a cylinder, a sphere, or a hemisphere. However, another shape such as a multiangular prism, a multiangular pyramid, a cone, an elliptic body, and a star-shaped prism may be designed and selected in consideration of a shape of the inlet portion. FIG. 3 and FIG. 4 show an embodiment of the case where a spherical shaped rigid portion 5a is provided between a central portion of the other side surface of an elastic portion 6 and an inner surface of a valve chamber 9. The rigid portion 5a is supported from the other end side by a base material 1 so as to be prevented from moving to the other end side. Furthermore, FIG. 5 and FIG. 6 show an embodiment of the case where a hemispherical shaped rigid portion 5b, which protrudes to one end side, is provided on a surface facing the other end surface of an elastic portion 6, and this rigid portion 5b is abutted on a central portion of the other end surface of the elastic portion 6. Also in these embodiments, each of the side surface abutting on the elastic portion 6 of the rigid portions 5a and 5b is dented into the other end surface of the elastic portion 6 to elastically deform the elastic portion 6 along the thickness direction thereof, to thereby press the elastic portion 6 against the one-way valve inlet portion 8 with a predetermined pressure. Thus, a function as a passive one-way valve V similar to the embodiment of FIG. 1 and FIG. 2 is obtained. Furthermore, also in these embodiments, the sum total of a diameter D2 of the rigid portion 5a or a protrusion amount P of the rigid portion 5b and a thickness W1 of the elastic portion 6 is set to be larger than a thickness W2 of the valve chamber 9.

It is preferable that the elastic portion 6 have a thickness of 50 μm or more and 2000 μm or less, more preferably, 100 μm or more and 1000 μm or less. If the elastic portion 6 has a thickness of less than 50 μm, the effect of the elastic force by the pressing of the rigid portion 5 is curbed. Therefore, there is a possibility that the hermeticity is decreased, making it difficult to control the pressing force on the one-way valve inlet portion 8. If the elastic portion 6 has a thickness of more than 2000 μm, not only the control of the pressing force by the rigid portion 5 becomes difficult, but also the microfluidic device becomes thicker. Therefore, this is not economical.

It is preferable that an elastic deformation amount 11 along the thickness direction of the elastic portion 6 (the pressed direction) as a result of the elastic portion 6 being pressed by the rigid portion 5 be 10 μm or more and 500 μm or less, more preferably 30 μm or more and 250 μm or less. If this amount is less than 10 μm, it is difficult to control the pressure and the pressing force on the elastic portion 6 when the one-way valve inlet portion 8 is hermetically sealed and the fluid is flowed. In addition, variations in the function of the one-way valve are likely to be produced depending on machining accuracy. If this amount exceeds 500 μm, it is difficult to control the pressure and the pressing force on the elastic portion 6 when the one-way valve inlet portion 8 is hermetically sealed and the fluid is flowed. In addition, the microfluidic device becomes thicker. Therefore, this is not economical.

Flow channels of a microfluidic devices with one of these passive one-way valves V are appropriately designed in consideration of a detection target and convenience. The microfluidic device can be made into a complex one with the provision of a film, a pump, a valve, a sensor, a motor, a mixer, a gear, a clutch, a micro lens, an electric circuit, or the like, or with a plurality of microchannels machined on the same substrate.

It is preferable that the base material 1 of the microfluidic device of the present invention be made of a plastic. As a material for plastic, the most preferable one is cyclic olefin copolymer (COC), which shows little autofluorescence and is recognized by FDA as a biomaterial (a material posing no problem when contacted with blood), in consideration of the fact that it is excellent in workability and economical efficiency and that the currently most commonly used detection method is fluorescence detection. However, it is possible to select one from among a variety of plastic materials. In consideration of moldability, heat resistance, chemical resistance, sorbability, and the like, it is appropriately selected according to the application and processing of the microchip to be fabricated, and the properties of the solvent, physiologically active substance, and detection method to be used. Examples thereof include: polystyrene, polyethylene, polyvinyl chloride, polypropylene, polycarbonate, polyester, polymethyl methacrylate, polyvinyl acetate, vinyl-acetate copolymer, styrene-methylmethacrylate copolymer, acrylic nitrile-styrene copolymer, acrylic nitrile-butadiene-styrene copolymer, nylon, polymethylpentene, silicon resin, amino plastic, polysulfone, polyether sulfone, polyetherimide, fluoroplastic, and polyimide. Furthermore, additives such as a pigment, a dye, an antioxidant, a fire retardant may be appropriately mixed into these plastic materials.

It is possible to immobilize a physiologically active substance in a part of a microchannel of the microfluidic device. Examples of the physiologically active substance include nucleic acid, protein, a sugar chain, and glycoprotein. The most suitable physiologically active substance can be appropriately selected according to the properties of the detection target. Furthermore, a plurality of physiologically active substances may be immobilized in the same channel. Moreover, a plurality of microchannels may be fabricated in the same microfluidic device, and a physiologically active substance may be immobilized in the respective microchannels. To immobilize a physiologically active substance on a surface of a microchannel of the microfluidic device, it is possible to subject the surface of the plastic to a surface modification such as: introduction of a functional group; immobilization of a functional material; addition of hydrophilicity; and addition of hydrophobicity.

Figure 7:
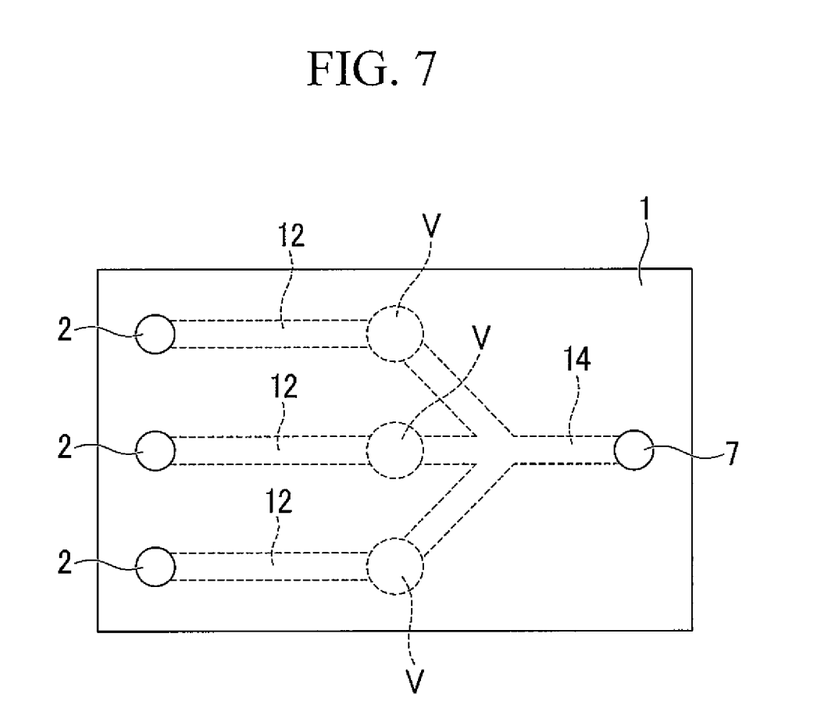
FIG. 7 is a plan view showing a fourth embodiment of a microfluidic device with a passive one-way valve of the present invention.

FIG. 7 shows an embodiment of such a microfluidic device. This microfluidic device is used for quantitative determination of antigen using the ELISA method. It has three inlets 2 in one end portion in a longitudinal direction of a base material 1, and one outlet 7 in the other end portion. Three microchannels 12 (first flow channels) extending from the respective inlets 2 are brought into one microchannel 14 (second flow channel) extending from the outlet 7. Furthermore, each of the microchannels 12 is provided with a passive one-way valve V. Moreover, in each of the microchannels 12, a reaction portion in which antigen is immobilized is provided in a site positioned between the inlet 2 and the passive one-way valve V, that is, in a site in communication with an inlet portion of the passive one-way valve V. In the microchannel 14, there is provided a detection portion for measuring absorbance of a fluid in the microchannel 14.

In quantitative determination of antigen, a sample including antigen with a known concentration is flowed into one of the three inlets 2 to allow an antigen-antibody reaction to occur in the reaction portion of the microchannel 12. The sample then reaches to the microchannel 14 via the passive one-way valve V, and the absorbance of the sample is measured in the detection portion. Subsequently, a sample including antigen with a known concentration different from that of the previously flowed sample is flowed into one of the remaining two inlets 2 to allow an antigen-antibody reaction to occur in the reaction portion. The absorbance of the sample is then measured in the detection portion. Then, the antigen concentrations and absorbances of these samples are used to create a calibration curve. Furthermore, a sample to be measured is flowed into the last one inlet 2 to allow an antigen-antibody reaction to occur in the reaction portion. The absorbance of the sample to be measured is then measured in the detection portion. The result is applied to the above calibration curve. Thereby, the antigen concentration in the sample to be measured is calculated.

In this type of microfluidic device, a passive one-way valve is provided between a reaction portion and a detection portion. Therefore, movement of fluid from the reaction portion to the detection portion is possible, whereas movement of fluid from the detection portion to the reaction portion is not possible. Consequently, continuous flow of fluid into the microchannel 12 does not allow the part of the fluid having passed through the passive one-way valve to reversely flow from the detection portion to the reaction portion. This makes it possible to detect a plurality of types (three types, in the embodiment shown in FIG. 7) of fluid according to the number of the microchannels 12 by use of the same detection portion. As a result, use of the same detection portion obtains an advantage in that a plurality of types of fluid can be detected with a small detection error. Furthermore, it obtains advantages in that it is not necessary to prepare a plurality of detectors according to the number of fluids to be tested, and that it is not necessary to position the microfluidic device and the detection portion thereof every time a detection is made.

EXAMPLE

Hereinafter is a specific description of the present invention by use of examples. However, the present invention is not limited to these examples at all.

In the examples below, tensile elasticity was measured using an "AUTOGRAPH AG-2000D" manufactured by Shimadzu Corporation as a tensile test machine, with a distance between the grip faces of 80 mm and a tensile speed of 20 mm/minute, in an atmosphere of room temperature of 24±1° C. and a humidity of 55±5%.

Example 1

As a base material, a plastic substrate made of cyclic olefin (ZEONOR 1060R manufactured by ZEON CORPORATION) was used. In it, an inlet and an outlet with a diameter of 1 mm, a microchannel with a width of 300 μm and a depth of 100 μm, a one-way valve inlet having an opening with a diameter of 300 μm, and a valve chamber with a diameter of 2 mm and a depth of 650 μm were fabricated by cutting work. Furthermore, as an elastic portion, silicone rubber with a tensile elastic modulus of about 1 MPa, a diameter of 2 mm, and a thickness of 500 μm was used. As a rigid portion, a wire made of SUS304 with a tensile elastic modulus of about 200 GPa, a diameter of 300 μm was used. Thus, a microfluidic device with the passive one-way valve shown in FIGS. 1 and 2 was fabricated.

When pure water was injected into the inlet from the inlet by use of a syringe, the pure water flowed out of the outlet. However, when injected from the outlet, the pure water did not flow out of the inlet. Therefore, this microfluidic device with the passive one-way valve functioned as a one-way valve.

Example 2

As a base material, an acrylic substrate was used. In it, an inlet and an outlet with a diameter of 1 mm, a microchannel with a width of 200 μm and a depth of 100 μm, a one-way valve inlet having an opening with a diameter of 200 μm, and a valve chamber with a diameter of 2 mm and a depth of 600 μm were fabricated by cutting work. Furthermore, for an elastic portion, silicone rubber with a tensile elastic modulus of about 1 MPa, a diameter of 2 mm, and a thickness of 500 μm was used. As a rigid portion, a polystyrene bead with a tensile elastic modulus of about 2 GPa, a diameter of 200 μm was used. Thus, a microfluidic device with the passive one-way valve shown in FIGS. 3 and 4 was fabricated.

When pure water was injected into the inlet from the inlet by use of a syringe, the pure water flowed out of the outlet. However, when injected from the outlet, the pure water did not flow out of the inlet. Therefore, this microfluidic device with the passive one-way valve functioned as a one-way valve.

Example 3

For a base material, a polycarbonate resin with a tensile elastic modulus of about 2.5 GPa was used. In it, an inlet and an outlet with a diameter of 1 mm, a microchannel with a width of 200 μm and a depth of 100 μm, a one-way valve inlet having an opening with a diameter of 200 μm, a valve chamber with a diameter of 2 mm and a depth of 250 μm, and a hemispherical protrusion as a rigid portion with a diameter of 200 μm and a protrusion amount of 100 μm were fabricated by injection molding. For an elastic portion, silicone rubber with a tensile elastic modulus of about 5 MPa, a diameter of 1 mm and a thickness of 200 μm was used. Thus, a microfluidic device with the passive one-way valve shown in FIGS. 5 and 6 was fabricated.

When pure water was injected into the inlet from the inlet by use of a syringe, the pure water flowed out of the outlet. However, when injected from the outlet, the pure water was did not flow out of the inlet. Therefore, this microfluidic device with the passive one-way valve functioned as a one-way valve.

Comparative Example 1

A microfluidic device with a passive one-way valve with the same configuration as that of Example 1 was fabricated, with the exception being that the material for the elastic portion was modified to polycarbonate with a tensile elastic modulus of about 25 GPa.

When pure water was injected into the inlet from the inlet by use of a syringe, the pure water flowed out of the outlet. Even when injected from the outlet, the pure water flowed out of the inlet. Therefore, this microfluidic device with the passive one-way valve did not function as a one-way valve.

Comparative Example 2

A microfluidic device with a passive one-way valve function with the same configuration as that of Example 1 was fabricated, with the exception being that the material for the rigid portion was modified to silicone rubber with a tensile elastic modulus of about 1 MPa.

When pure water was injected into the inlet from the inlet by use of a syringe, the pure water flowed out of the outlet. Even when injected from the outlet, the pure water flowed out of the inlet. Therefore, this microfluidic device with the passive one-way valve did not function as a one-way valve.

INDUSTRIAL APPLICABILITY

By utilizing the present invention, it is possible to provide a simple and inexpensive passive one-way valve without requiring special equipment such as a vacuum pump and a pressurized air, and to provide a microfluidic device using the same.

The invention claimed is:

1. A passive one-way valve for use in a connection portion between first and second flow channels, comprising:
    an inlet portion into which a fluid from the first flow channel flows;
    an elastic portion for blocking the inlet portion at one surface thereof;
    a rigid portion configured to support the elastic portion at the other surface of the elastic portion from a side opposite to the inlet portion across the elastic portion;
    a gap portion formed around the rigid portion; and
    an outlet portion which is in communication with the gap portion for letting the fluid flow out into the second flow channel, wherein
    the inlet portion is operable to be hermetically sealed by the elastic portion being pressed against a side of the inlet portion by the rigid portion without deformation of the rigid portion.

2. The passive one-way valve according to claim 1, wherein
    the elastic portion is made of a material with a tensile elastic modulus of 0.1 MPa or more and 700 MPa or less, and the rigid portion is made of a material with a tensile elastic modulus of 0.5 GPa or more.

3. The passive one-way valve according to claim 1, wherein
    the elastic portion is pressed by the rigid portion over an area 0.5 or more times and 1.5 or less times that of an opening portion of the inlet portion.

4. The passive one-way valve according to claim 1, wherein
    the rigid portion has a cylindrical, spherical, or hemispherical shape.

5. The passive one-way valve according to claim 1, wherein
    the elastic portion has a thickness of 50 µm or more and 2000 µm or less.

6. The passive one-way valve according to claim 1, wherein
    an elastic deformation amount of the elastic portion caused by the elastic portion being pressed by the rigid portion is 10 µm or more and 500 µm or less with respect to a pressed direction.

7. A microfluidic device according to claim 1, having a plurality of flow channels in communication with one another in a connection portion, wherein
    the connection portion is provided with the passive one-way valve.

8. The microfluidic device according to claim 7, wherein a base material is made of a plastic.

9. The microfluidic device according to claim 7, wherein a physiologically active substance, which includes at least one of nucleic acid, protein, a sugar chain, and glycoprotein is immobilized in part of the flow channel.

10. The microfluidic device according to claim 9, wherein the physiologically active substance is immobilized in the flow channel which is in communication with the inlet portion of the passive one-way valve.

11. The passive one-way valve according to claim 1, wherein the inlet portion, the elastic portion, and the rigid portion are arranged in order on the axial line of the inlet portion.

12. The passive one-way valve according to claim 11, wherein the axial line of the inlet portion is substantially perpendicular to an axial line of the outlet portion.

13. The passive one-way valve according to claim 1, wherein the inlet portion is hermetically sealed by the elastic portion being pressed against the side of the inlet portion by the rigid portion denting into the elastic portion.

14. The passive one-way valve according to claim 1, further comprising:
    a valve chamber communicated with the first flow channel and the second flow channel, and the elastic portion, the rigid portion, and the gap portion disposed in the valve chamber, wherein
    a sum total of a diameter of the rigid portion and a thickness of the elastic portion is larger than a thickness of the valve chamber.

15. The passive one-way valve according to claim 14, wherein the rigid portion is configured to be supported by a base material in which the first flow channel and the second flow channel at one side of the base material so as to be prevented from moving to the one side of the base material, and configured to be elastically deformed along a direction of the thickness of the elastic portion by a contacted surface of the rigid portion denting into one surface of the elastic portion.

16. The passive one-way valve according to claim 1, wherein a shape of the rigid portion is a multiangular prism, a multiangular pyramid, a cone, an elliptic body, or a star-shaped prism.

17. The passive one-way valve according to claim 1, wherein a material of the rigid portion is metal or plastic.

* * * * *

UNITED STATES PATENT AND TRADEMARK OFFICE
CERTIFICATE OF CORRECTION

PATENT NO.       : 8,545,767 B2                                                Page 1 of 1
APPLICATION NO. : 12/160593
DATED            : October 1, 2013
INVENTOR(S)      : Susumu Arai It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 713 days.

Signed and Sealed this

Fifteenth Day of September, 2015

Michelle K. Lee
*Director of the United States Patent and Trademark Office*